United States Patent [19]
// Hughes

[11] Patent Number: 5,625,080
[45] Date of Patent: Apr. 29, 1997

[54] BENZODIFURANTRIONE COMPOUNDS AND PROCESS

[75] Inventor: Nigel Hughes, Oldham, Great Britain

[73] Assignee: Zeneca Limited, London, England

[21] Appl. No.: 446,638

[22] PCT Filed: Nov. 11, 1993

[86] PCT No.: PCT/GB93/02318

§ 371 Date: May 25, 1995

§ 102(e) Date: May 25, 1995

[87] PCT Pub. No.: WO94/12501

PCT Pub. Date: Jun. 9, 1994

[30] Foreign Application Priority Data

Nov. 25, 1992 [GB] United Kingdom .................. 9224647
Nov. 25, 1992 [GB] United Kingdom .................. 9224649
Jan. 25, 1993 [GB] United Kingdom .................. 9301422

[51] Int. Cl.$^6$ .................................................. C07D 407/00
[52] U.S. Cl. ................................................................ 549/299
[58] Field of Search .................................................. 549/299

[56] References Cited

FOREIGN PATENT DOCUMENTS 33583 8/1981 European Pat. Off. .
252406 1/1988 European Pat. Off. .

*Primary Examiner*—Amelia Owens
*Attorney, Agent, or Firm*—Cushman Darby & Cushman IP Group Pillsbury Madison & Sutro LLP

[57] ABSTRACT

Benzodifurantriones of Formula (1):

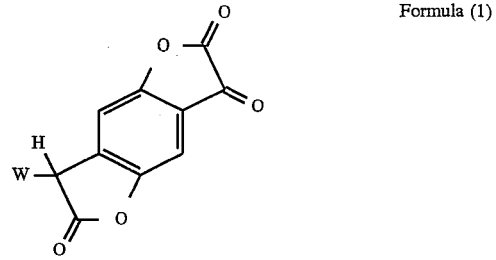

Formula (1)

in which W is unsubstituted or substituted aryl, a process for their preparation via dioxo intermediates and processes for their conversion into benzodifuranone dyes and compounds of Formula (7):

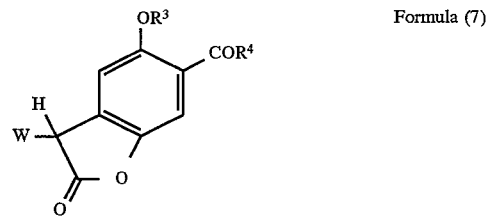

Formula (7)

are provided wherein $R^3$ is —H, —COR$^2$, —SO$_2$R$^2$— which R$^2$ is alkyl, cycloalkyl, aryl or aralkyl and R$^4$ is —COOR$^2$, —CONRR$^1$ in which R and R$^1$ each independently is —H, alkyl, cycloalkyl, aryl or aralkyl; —COOH or the alkali metal, alkaline earth metal or ammonium salts thereof; or —COX$^2$— which X$^2$ is halo.

10 Claims, No Drawings

BENZODIFURANTRIONE COMPOUNDS AND PROCESS

The present invention relates to benzodifurantriones and their tautomeric forms, to a process for their preparation, to intermediate acid chlorides, to processes for the preparation of benzodifuranones, to intermediate benzofuranones and to a process for the preparation of benzofuranones.

According to a first feature of the present invention there is provided a benzodifurantrione of Formula (1):

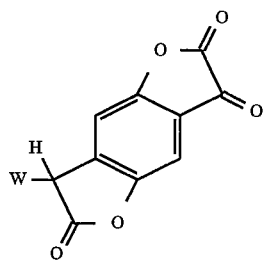

Formula (1)

wherein:

W is unsubstituted or substituted aryl.

Examples of suitable substituent groups for W are alkyl; alkenyl; alkoxy; alkoxyalkyl; alkoxyalkoxy; alkylcarbonyl; alkoxycarbonyl; alkoxycarbonylalkoxy; alkoxyalkoxycarbonylalkoxy; alkylcarbonyloxyalkoxy; cyanoalkyl; cyanoalkoxy; hydroxyalkyl; hydroxyalkoxy; haloalkyl, especially fluoro-, chloro- or bromoalkyl; haloalkoxy, especially fluoro-, chloro- or bromoalkoxy; alkylthio; arylthio; aryloxy; alkylsulphonyl; arylsulphonyl; halo, especially chloro or bromo; hydroxy; cyano; nitro; amino; alkylamino; dialkylamino; cycloalkylamino; alkylcarbonylamino; arylcarbonylamino; alkylsulphonylamino; arylsulphonylamino; cycloalkyl; and alkylamino and dialkylamino substituted by —CN, —Cl, —F, —Br, —OH, —COOC$_{1-4}$-alkyl, —COOC$_{1-4}$-alkylOC$_{1-4}$-alkyl, -phenyl, —OCOC$_{1-4}$-alkyl; and preferably such groups in which the alkyl or alkoxy contains from 1 to 8 carbon atoms, especially from 1 to 4 carbon atoms; the alkenyl contains from 2 to 6 carbon atoms, especially from 2 to 4 carbon atoms; the aryl is phenyl or naphthyl and the cycloalkyl contains from 3 to 8 carbon atoms, more preferably from 4 to 6 carbon atoms and especially 6 carbon atoms. Each alkyl, alkoxy or alkenyl may be straight or branched chain alkyl or alkoxy respectively.

W is preferably naphthyl or phenyl, more preferably a group of formula:

wherein:

Ring A is unsubstituted or is substituted by from 1 to 5 groups.

Preferred substituent groups for Ring A are selected from C$_{1-4}$-alkyl, C$_{1-4}$-alkoxy, hydroxy, C$_{1-4}$-alkoxy-C$_{1-4}$-alkoxycarbonylC$_{1-4}$-alkoxy, amino, C$_{1-4}$-alkylamino and (C$_{1-4}$-alkyl)$_2$amino and combinations thereof.

Ring A is preferably unsubstituted or is substituted by from one to three groups. Where one substituent group is present in Ring A this is preferably in the 4-position, where two substituent groups are present in Ring A these are preferably in the 3- and 4-positions and where three substituent groups are present in Ring A these are preferably in the 3-, 4- and 5-positions.

The benzodifurantriones of Formula (1) may exist in a number of tautomeric forms, for example in forms represented by Formulae (1A) and (1B):

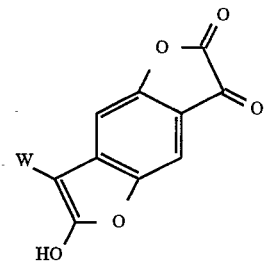

Formula (1A)

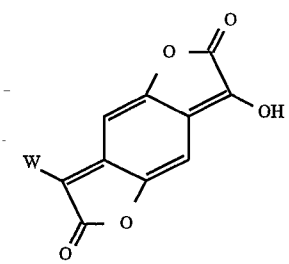

Formula (1B)

and it is intended that the structure represented by Formula (1) includes all tautomeric forms.

According to a further feature of the present invention there is provided a process for the preparation of a benzodifurantrione of Formula (1) by reacting a compound of Formula (2):

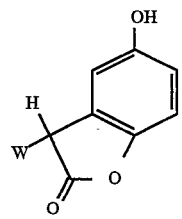

Formula (2)

with a compound of Formula (3):

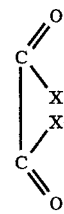

Formula (3)

wherein:

W is as hereinbefore defined; and X and X$^1$ each independently is halo; —Oalkyl; —OH; —NH$_2$; —NHalkyl and —N(alkyl)$_2$.

The halo group represented by X and X$^1$ is preferably —Cl, —Br or —I and more preferably —Cl or —Br. The —Oalkyl group represented by X and X$^1$ is preferably —OC$_{1-6}$-alkyl, more preferably —OC$_{1-4}$-alkyl and especially —OCH$_3$ or —OC$_2$H$_5$. The —NHalkyl group represented by X and X$^1$ is preferably —NHC$_{1-6}$-alkyl and more preferably —NHC$_{1-4}$-alkyl. The —N (alkyl)$_2$ group represented by X and X$^1$ is preferably —N (C$_{1-6}$-alkyl)$_2$ and more preferably —N(C$_{1-4}$-alkyl)$_2$.

X and X$^1$ are preferably —Cl or —Br.

The reaction of the compound of Formula (2) with the compound of Formula (3) may occur in one or in two stages depending on the reaction conditions used.

In a two stage reaction a compound of Formula (2) is firstly reacted with a compound of Formula (3) to form a compound of Formula (4):

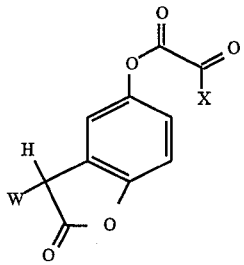

Formula (4)

wherein:

W and X are as hereinbefore defined.

The first stage of this reaction is preferably performed in the presence of a catalyst. The catalyst is preferably a non-nucleophilic base, more preferably a tertiary amine and especially triethylamine, pyridine, 2-dimethylaminopyridine, 4-dimethylaminopyridine or dimethylformamide. The catalyst is preferably present at 0.1 to 5.0% by weight of the compound of Formula (2).

The compound of Formula (4) may, if desired, be isolated by removal of the reaction medium by distillation optionally under reduced pressure or the reaction mixture may be used without further treatment in the second stage of the reaction.

In the second stage the compound of Formula (4) may be cyclised to the benzodifurantrione of Formula (1) in the presence of a non-nucleophilic base, preferably tertiary amine such as triethylamine, tripropylamine, tributylamine, N,N-diisopropylethylamine, diazabicyclooctane or pyridine, a quaternary ammonium compound such as N-ethylpyridine, an alkali metal carbonate such as potassium carbonate, a sulphoxide such as dimethylsulphoxide, or an alkali metal alkoxide such as potassium t-butoxide.

The ratio of non-nucleophilic base to the compound of Formula (4) is preferably from 2:1 to 10:1, more preferably from 2:1 to 5:1 and especially from 2:1 to 3:1.

An acid binder may be added to the second stage of the process, suitable acid binders are inorganic carbonates, bicarbonates, oxides and acetates such as sodium, potassium or calcium carbonate, sodium or potassium bicarbonate, magnesium, calcium or bismuth oxide or potassium acetate.

In a one stage reaction a compound of Formula (2) is reacted with a compound of Formula (3) in the presence of a non-nucleophilic base and optionally in the presence of an acid binder. Suitable non-nucleophilic bases and acid binders are those described above. In a one stage reaction the ratio of non-nucleophilic base to the compound of Formula (1) is preferably from 1:1 to 10:1, more preferably from 1:1 to 5:1 and especially from 1:1 to 3:1. Where an acid binder is used in combination with a non-nucleophilic base a total of at least 3 molar equivalents of binder and base to the compound of Formula (2) are required.

The one or two stage reactions of the present invention may be performed by heating the reactants in a liquid medium, preferably an inert liquid medium, more preferably in a dry inert liquid medium and especially in an aliphatic hydrocarbon such as hexane, or an aromatic hydrocarbon such as benzene, toluene or xylene, or a halogenated aliphatic hydrocarbon such as dichloromethane, chloroform or dichloroethane, or a halogenated aromatic hydrocarbon such as chlorobenzene or 1,2-dichlorobenzene, or an ether such as diethyleneglycol, dimethylether, diethylether or tetrahydrofuran, or an ester such as ethylacetate or an amide such as dimethylformamide or a ketone such as acetone.

The one or two stage reactions of the process are preferably performed at a temperature of from 20° C. to 180° C., more preferably at from 30° C. to 120° C., especially at from 40° C. to 80° C. and conveniently at the reflux temperature of the liquid medium used.

The benzodifurantrione of Formula (1) may be isolated by cooling the reaction mixture and pouring into water followed by distillation to remove the liquid medium and separation, by for example filtration, of the product from the remaining aqueous material.

The cyclisation of the compound of Formula (4) to the benzodifurantrione of Formula (1) may also be performed under Friedel Craft's conditions where the acid chloride is heated in the presence of a Lewis acid such as aluminium chloride, iron (III) chloride, zinc chloride or borontrifluoride in a dry inert liquid medium preferably in an aliphatic hydrocarbon such as hexane, an aromatic hydrocarbon such as toluene or xylene, a halogenated aliphatic hydrocarbon such as dichloromethane or dichloroethane or a halogenated aromatic hydrocarbon such as chlorobenzene or 1,2-dichlorobenzene. This cyclisation is preferably performed at a temperature from 20° C. to 120° C. and conveniently at the reflux temperature of the liquid medium used. The product may be isolated by cooling the reaction mixture and pouring into a mixture of ice and water followed by separation and evaporation the liquid medium.

The compound of Formula (2) may be prepared as described in GB 2068402A by reaction of hydroquinone or dihydroxybenzene with an optionally substituted mandelic acid at an elevated temperature in the presence of an acid catalyst followed by pouring the reaction mixture into water and collecting the precipitated product by filtration.

The compound of Formula (4) is novel and accordingly this forms a further feature of the present invention, there is provided a compound of the Formula (4):

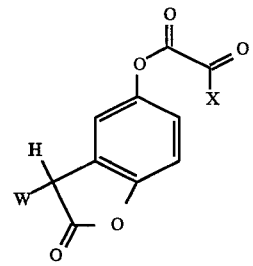

Formula (4)

wherein:

W and X are as hereinbefore defined.

According to a further feature of the present invention there is provided a process for the preparation of a compound of the Formula (5):

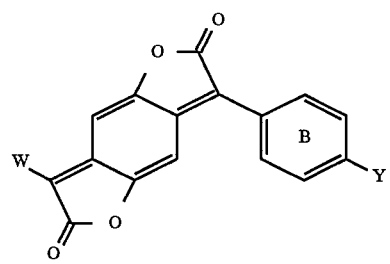

Formula (5)

by reacting a benzodifurantrione of the Formula (1) with a compound of Formula (6):

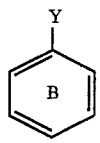

Formula (6)

wherein:

Ring B is unsubstituted, apart from the group Y, or is substituted by one or two further groups;

Y is an electron rich activating group; and

W is as hereinbefore defined.

Examples of substituents for Ring B are those described above for W. Where Ring B is substituted by one further group this is preferably in the 3-position i.e. adjacent the group Y, where Ring B is substituted by two further groups these are preferably in the 3- and the 5-positions i.e. both adjacent the group Y.

The electron rich activating group represented by Y is preferably —OR, —NRR$^1$, —SR, —NHCOR$^2$ and —NHSO$_2$R$^2$ in which R and R$^1$ each independently is —H or -alkyl, cycloalkyl, aryl or aralkyl, each of which may be optionally substituted and R$^2$ is -alkyl, cycloalkyl, aryl or aralkyl each of which may be optionally substituted; or where Y is —NRR$^1$, R and R$^1$ together with the N atom to which they are attached form a heterocyclic group such as a piperidino or morpholino group; or where Y is —NRR$^1$ one of R or R$^1$ together with the carbon atom of Ring B to which Y is attached and the adjacent carbon atom on Ring B form a bicyclic group such as a tetrahydroquinolinyl or indolyl group with Ring B. Where the groups represented by R, R$^1$ or R$^2$ are substituted, examples of preferred substituents are hydroxy, chloro, bromo, nitro, cyano and $C_{1-4}$-alkoxy.

The alkyl group represented by R, R$^1$ or R$^2$ is preferably $C_{1-6}$-alkyl and more preferably $C_{1-4}$-alkyl, the aryl group represented by R, R$^1$ or R$^2$ is preferably phenyl and the aralkyl group represented by R, R$^1$ or R$^2$ is preferably aryl-$C_{1-4}$-alkyl and more preferably benzyl. Each alkyl may be straight or branched chain alkyl.

This process may be performed by heating the reactants in the presence of an acid condensing agent optionally in a liquid medium. The acid condensing agent is preferably an inorganic acid, more preferably a mineral acid such as sulphuric acid, or an organic acid, more preferably an alkanecarboxylic acid such as acetic or propionic acid or an alkyl- or arylsulphonic acid such as methanesulphonic, toluenesulphonic or dodecylbenzenesulphonic acid. The liquid medium is preferably an inert organic liquid, more preferably an aromatic hydrocarbon such as toluene or xylene or a halogenated aromatic hydrocarbon such as chlorobenzene or 1,2-dichlorobenzene or is any of the acid condensing agents described above or is a combination of one or more of the condensing agents and/or one or more of the liquid media.

The process is preferably performed at a temperature from 50° C. to 180° C. and more preferably at 70° C. to 160° C. and where a suitable liquid medium is present conveniently under reflux.

The compounds of Formula (5) in which Y is —OH or in which A carries a hydroxy may be reacted further with for example alkylating, acylating or sulphonylating agents to produce Oalkyl, Oacyl and Osulphonyl derivatives respectively.

According to a further feature of the present invention there is provided a process for the preparation of a compound of the Formula (5) by reacting a benzofuranone of Formula (7):

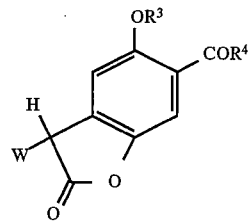

Formula (7)

with a compound of Formula (6)

wherein:

W, Ring B and Y are as hereinbefore defined;

R$^3$ is —H, —COR$^2$, —SO$_2$R$^2$, in which R$^2$ is as hereinbefore defined; and R$^4$ is —COOR$^2$ in which R$^2$ is as hereinbefore defined; —CONRR$^1$ in which R and R$^1$ are as hereinbefore defined; —COOH or the alkali metal, alkaline earth metal or ammonium salts thereof; or —COX$^2$ in which X$^2$ is halo.

Where the group represented by R$^4$ is the alkali metal salt of —COOH the alkali metal is preferably lithium, sodium or potassium, more preferably sodium or potassium, where R$^4$ is the alkaline earth metal salt of —COOH the alkaline earth metal is preferably magnesium or calcium, where R$^4$ is the ammonium salt of —COOH the ammonium may be NH$_4^+$ or a mono-, di-, tri or tetraalkyl substituted ammonium where the alkyl contains from 1 to 10 carbon atoms. The halogen represented by X$^2$ in the group —COX$^2$ is preferably bromo or chloro, more preferably chloro.

This process may be performed by heating the reactants optionally in the presence of an acid condensing agent and optionally in the presence of a liquid medium.

The acid condensing agent is preferably an inorganic acid, more preferably a mineral acid such as sulphuric acid, or an organic acid, more preferably an alkanecarboxylic acid such as acetic or propionic acid or an alkyl- or arylsulphonic acid such as methanesulphonic, toluenesulphonic or dodecylbenzenesulphonic acid. The liquid medium is preferably an inert organic liquid, more preferably an aromatic hydrocarbon such as toluene or xylene or a halogenated aromatic hydrocarbon such as chlorobenzene or 1,2-dichlorobenzene or is any of the acid condensing agents described above or is a combination of one or more of the condensing agents and/or one or more of the liquid media.

The process is preferably performed at a temperature from 50° C. to 180° C. and more preferably at 70° C. to 160° C. and where a suitable liquid medium is present conveniently under reflux.

The compound of Formula (5) may be isolated from the reaction mixture by any convenient means, for example by filtration of the reaction mixture. The compound of Formula (5) may be purified by any convenient means such as washing with a suitable liquid such as methanol or water or by crystallisation from a suitable organic liquid such as an alcohol, for example methyl, ethyl, propyl alcohols, 2-methoxyethanol, an amide for example dimethyl formamide, or a haloaromatic for example chloro- or dichlorobenzene.

According to a further feature of the present invention there is provided a compound of Formula (7):

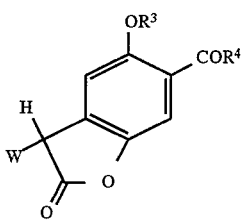

Formula (7)

wherein W, R³ and R⁴ are as hereinbefore defined.

According to a further feature of the present invention there is provided a process for the preparation of a compound of Formula (7) by reaction of a compound of Formula (1) with ZH in which Z is —OH, —OR², —NRR$^1$ or X² in which R, R$^1$, R$^2$ and X² are as hereinbefore defined.

This process may be performed by mixing the reactants optionally in the presence of a liquid medium. Suitable liquid media may be water or any of the inert organic liquids described above. Reactions of compound of Formula (1) with water, i.e. where Z is —OH, may be performed in an alkaline solution. Suitable alkaline solutions include an aqueous solution of an alkali metal or ammonium hydroxide such as sodium hydroxide or potassium hydroxide aqueous solutions of alkali metal carbonates such as sodium or potassium carbonate.

The process is preferably performed at a temperature of from 0° C. to 100° C., more preferably at from 10° C. to 60° C. and especially at from 10° C. to 30° C.

The compound of Formula (7) may be isolated from the reaction mixture by any convenient means, for example by filtration of the reaction mixture.

The compounds of Formulae (1), (4) and (7) are useful as intermediates for the preparation of a variety of organic compounds particularly for use as intermediates in the manufacture of dyes, agrochemicals and pharmaceuticals. The compounds of Formula (5) may be used as dyes particularly for the coloration of synthetic textile materials such as polyester.

The invention is further illustrated by the following examples.

EXAMPLE 1

Oxalyl chloride (2.6 parts) and 4-dimethylaminopyridine (0.1 parts) were added to a suspension of 5-hydroxy-2-oxo-3-phenyl-2,3-dihydrobenzofuran (4.52 parts) in dry dichloromethane (50 parts). The mixture was stirred and heated under reflux, for approximately 6 hours, until the evolution of hydrogen chloride gas ceased. The mixture was cooled to 20° C. and a solution of triethylamine (5 parts) in dry dichloromethane (25 parts) was added dropwise, with stirring, over 5 minutes. The mixture was refluxed for a further 3 hours before cooling and pouring into water (100 parts) and adding 2M hydrochloric acid (20 parts). The methylene chloride was removed by distillation to leave the product as a brown crystalline solid suspended in water. The product was collected by filtration and dried to give 7-phenyl-7-hydro-2,3,6-trioxo-benzo [1:2-b, 4:5-b']difuran (5.3 parts, 94.6%). The product was purified by recrystallisation from acetonitrile (λmax=552 nm, εmax=35,000 in dimethylformamide).

EXAMPLE 2

By the method of Example 1.

Oxalyl chloride (1.3 parts) and 2-dimethylaminopyridine (0.05 parts) were added to a suspension of 5-hydroxy-2-oxo-3-(4-methoxyphenyl)-2,3-dihydrobenzofuran (2.56 parts) in dichloromethane (25 parts).

The product 7-(4-methoxyphenyl)-7-hydro-2,3,6-trioxobenzo(1:2-b,4:5-b')difuran (3.26 parts; 105%). Purified by trituration and washing with dichloromethane. λmax 552 nm εmax 28,680 in dimethylformamide.

EXAMPLE 3

By the method of Example 2.

5-hydroxy-2-oxo-3-(4-ethoxyphenyl)-2,3-dihydrobenzofuran (2.7 parts) reacted to give the product 7-(4-ethoxyphenyl)-7-hydro-2,3,6-trioxo-benzo(1:2-b,4:5-b')difuran (3.25 parts; 100%).

Purified product λmax 562 nm εmax 31,429 in dimethylformamide.

EXAMPLE 4

By the method of Example 2.

5-hydroxy-2-oxo-3-(4-propoxyphenyl)-2,3-dihydrobenzofuran (2.84 parts) reacted to give the product 7-(4-propoxyphenyl)-7-hydro-2,3,6-trioxo-benzo(1:2-b,4:5-b')difuran (3.53 parts; 104%).

Purified product λmax 562 nm εmax 25,623 in dimethylformamide.

EXAMPLE 5

By the method of Example 2.

Oxalyl chloride (3.9 parts) and 2-dimethylaminopyridine (0.1 parts) were added to a suspension of 5-hydroxy-2-oxo-3-(4-butoxyphenyl)-2,3-dihydrobenzofuran (8.49 parts) in dichloromethane (75 parts).

The product 7-(4-butoxyphenyl)-7-hydro-2,3,6-trioxobenzo(1:2-b,4:5-b')difuran (11.35 parts 107.5%)

Purified product λmax 561 nm εmax 35,159 in dimethylformamide, analysis C,68.2; H4.5; C20H16O6 requires C,68.2; H,4.5%. Mass Spectrometry shows a molecular ion at 352 together with fragmentation consistent with structure.

EXAMPLE 6

By the method of Example 2.

5-hydroxy-2-oxo-3-(4-iso propoxyphenyl)-2,3-dihydrobenzofuran (2.84 parts) reacted to give the product 7-(4-iso propoxyphenyl)-7-hydro-2,3,6-trioxo-benzo(1:2-b, 4:5-b')difuran (3.72 parts 110%).

Purified product λmax 561 nm εmax 29,583 in dimethylformamide.

EXAMPLE 7

By the method of Example 2.

Oxalyl chloride (0.65 parts) and 2-dimethylaminopyridine (0.05 parts) were added to a suspension of 5-hyroxy-2-oxo-3-(4-methylphenyl)-2,3-dihydrobenzofuran (1.2 parts) in dichloromethane (15 parts).

The product 7-(4-methylphenyl)-7-hydro-2,3,6-trioxobenzo(1: 2-b,4:5-b')difuran (1.7 parts 115%).

Purified product λmax 555.6 nm εmax 29,208 in dimethylformamide. Mass Spectrometry shows a molecular ion at 294 together with fragmentation consistent with structure. $^1$H and $^{13}$Cnmr both consistent with structure.

EXAMPLE 8

By the method of Example 2.

5-hydroxy-2-oxo-3-(3-methylphenyl)-2,3-dihydrobenzofuran (2.4 parts) reacted to give the product 7-(3-methylphenyl)-7-hydro-2,3,6-trioxo-benzo(1:2-b,4:5-b')difuran (2.8 parts; 95%).

Purified product λmax 554 nm εmax 34,000 in dimethylformamide. Mass Spectrometry shows a molecular ion at 294 together with fragmentation consistent with structure. $^1$H and $^{13}$Cnmr both consistent with structure.

EXAMPLE 9

By the method of Example 2.

5-hydroxy-2-oxo -3-(3,4-dimethoxyphenyl)-2,3-dihydrobenzofuran (2.86 parts) reacted to give the product 7-(3,4-dimethoxy)-7-hydro-2,3,6-trioxo-benzo(1:2-b,4:5-b')difuran (2.7 parts; 80%).

Purified product was a mixture. Mass Spectrometry shows a molecular ion at 340 consistent with the required structure.

EXAMPLE 10

By the method of Example 2.

Oxalyl bromide (3.3 parts) and 2-dimethylaminopyridine (0.125 parts) were added to a suspension of 5-hydroxy-2-oxo-3-phenyl-2,3-dihydrobenzofuran (5.65 parts) in dichloromethane (50 parts).

The product after purification was identical to that obtained in Example 1.

EXAMPLE 11

Oxalyl chloride (17.5 parts) and pyridine (0.5 parts) were added to a suspension of 5-hydroxy-2-oxo-3-phenyl-2,3-dihydrobenzfuran (22.6 parts) in dichloromethane (200 parts). After six hours reflux, chloro-oxo-acetic acid 2-oxo-3-phenyl-2,3-dihydro-benzofuran-5-yl ester was isolated and phenol (9.9 parts) added and the mixture refluxed for eighteen hours. Removal of the solvent gave the crude product oxalic acid (2-oxo-3-phenyl-2,3-dihydro-benzofuran-5-yl)ester phenyl ester (33.3 parts; 89%). Trituration in methanol and recrystallisation from ethyl acetate gave a pure product. Analysis C,70.4; H,3.7; C22H13O6 requires C,70.8; H,3.5%. M.pt.134° C., $^1$H and $^{13}$Cnmr gave spectra consistent with structure.

Subsequent cyclisation in dichloromethane with triethylamine and purification gave a product identical to that obtained in Example 1.

EXAMPLE 12

Reaction of chloro-oxo-acetic acid 2-oxo-3-phenyl-2,3-dihydro-benzofuran-5-yl ester prepared as Example 11 reacted in toluene at the reflux with p-nitrophenol gave after purification oxalic acid (4-nitro-phenyl) ester (2-oxo-3-phenyl-2,3-dihydro-benzofuran-5-yl) ester (33% yield). Analysis C,63.5; H,3.3; N,3.5; C22H13NO8 requires C,63.0; H,3.1; N,3.3%. Mass Spectrometry shows a molecular ion at 419.

Subsequent cyclisation in dichloromethane with triethylamine and purification gave the product obtained in Example 1.

EXAMPLE 13

Reaction of chloro-oxo-acetic acid 2-oxo-3-phenyl-2,3-dihydro-benzofuran-5-yl ester prepared as Example 11 reacted in toluene at the reflux with 2,6-dimethylphenol gave after purification oxalic acid (2,6-dimethyl-phenyl) ester (2-oxo-3-phenyl-2,3-dihydro-benzofuran-5-yl) ester (38% yield). Analysis C,70.6; H,4.1; C24H18O6 requires C,71.8; H,4.2%. Mass Spectrometry shows a molecular ion at 402.

Subsequent cyclisation in dichloromethane with triethylamine and purification gave the product obtained in Example 1.

EXAMPLE 14

Preparation of di-(2-oxo-3-phenyl-2,3-dihydrobenzofuran-5-oxy) oxalate

Method A

5-Hydroxy-2-oxo-3-phenyl-2,3-dihydrobenzofuran (23 parts) and oxalyl chloride (65 parts) were added to dichloromethane (1990 parts) under a nitrogen atmosphere. A solution of dimethylformamide (7.3 parts) in dichloromethane (133 parts) was added dropwise over 30 minutes. The solution was heated to reflux for 21 hours and then cooled to ambient. Further oxalyl chloride (65 parts) was added followed by more dimethylformamide (7.3 parts) in dichloromethane (133 parts). The solution was heated to reflux again for 24 hours. After cooling to ambient temperature, the reaction mixture was washed with water (500 parts) and the solvent was distilled under vacuum. Slurrying the brown tarry residue with methanol yielded di-(2-oxo-3-phenyl-2,3-dihydrobenzofuran-5-oxy) oxalate (132 parts) as an off-white solid. The $^1$Hnmr, $^{13}$Cnmr, mass and infrared spectra of the purified product were consistent with the structure.

Method B

5-Hydroxy-2-oxo-3-phenyl-2,3-dihydrobenzofuran (464 parts), oxalyl chloride (305 parts), toluene (347 parts) and 2-dimethylaminopyridine (7 parts) were added to dichloromethane (10600 parts) under a nitrogen atmosphere. The suspension was heated to reflux temperature for 2.5 hours. After cooling to ambient temperature, further 5-hydroxy-2-oxo-3-phenyl-2,3-dihydrobenzofuran (464 parts) in dichloromethane (5300 parts) containing triethylamine (202 parts) was added over 1 hour, and the purple coloured solution was stirred overnight at ambient temperature. After washing with cold water, the solvent was distilled under vacuum to give a purple coloured solid (1120 parts). Recrystallisation from ethyl acetate gave di-(2-oxo-3-phenyl-2,3-dihydrobenzofuran-5-oxy) oxalate (559 parts), which was identical to the sample prepared by Method A.

EXAMPLE 15

Preparation of 7-phenyl-7-hydro-2,3,6-trioxo-benzo [1:2-b,4:5-b,]difuran

Di-(2-oxo-3-phenyl-2,3-dihydrobenzofuran-5-oxy) oxalate (60 parts) was dissolved in dimethylacetamide (470 parts), toluene (44 parts), triethylamine (20 parts) and 49 parts of a 1% w:v solution of 2-dimethylaminopyridine in dichloromethane. The solution was heated at 80° C. for 2 hours. Methane-sulfonic acid (19 parts) was added to the cooled reaction mixture and the volatiles were removed (75° C./1.0 mmHg). The resulting dark red tar (107 parts) was dissolved in dichloromethane (1325 parts), washed with water, separated and the solvent removed from the organic phase to give crude product oil (74 parts). Crystallisation from ethyl acetate gave a dark red solid (18 parts), identical (by gas and liquid chromatography and $^1$Hnmr) to a sample of 7-phenyl-7-hydro-2,3,6-trioxo-benzo[1:2-b,4:5-b'] difuran prepared by Method A.

EXAMPLE 16

Preparation of Di-(2-oxo-3-(2,5-dimethylphenyl)-2,3-dihydrobenzofuran-5-oxy) oxalate i) 5-hydroxy-2-oxo-3-(2,5-dimethylphenyl)-2,3-dihydrobenzofuran The method used to prepare 2,5-dimethylmandelic acid was similar to that described by Riebsomer and Irvine (Org.Synth.,Coll.Vol.3, p.327). Thus, ethyl oxomalonate (25 parts) in para-xylene (38 parts) was stirred at 0°–5° C. under a nitrogen atmosphere as anhydrous stannic chloride (46 parts) was charged over 20 minutes. The mixture was kept mobile by addition of further para-xylene (43 parts) and allowed to warm to ambient temperature. After 3 hours stirring, the mixture was quenched on a mixture of ice and 10M hydrochloric acid and extracted into diethyl ether. The separated organic phase was washed with water, dried over magnesium sulfate, filtered and the solvent was evaporated under reduced pressure. The crude brown oil (31 parts) was then distilled under vacuum to give diethyl (2,5-dimethylphenyl)-hydroxymalonate (26 parts). $^1$Hnmr, $^{13}$Cnmr and mass spectra and micro-analysis were all consistent with the structure.

A sample of the diethyl (2,5-dimethylphenyl)-hydroxymalonate (21 parts) was reacted with a solution of potassium hydroxide (21 parts) in water (84 parts) at 98° C. for 5 hours. After cooling to ambient temperature, the reaction was washed with diethyl ether and acidified with 10M hydrochloric acid. After heating to 98° C. for a further 2 hours, the cooled materials was extracted into diethyl ether. The separated organic phase was dried over magnesium sulfate, filtered and the solvent was evaporated under reduced pressure. The crude amber coloured oil (15 parts) solidified on standing. Recrystallisation from toluene gave 2,5-dimethylmandelic acid (7 parts). The $^1$Hnmr, $^{13}$Cnmr and mass spectra were all consistent with the structure.

By the method described in GB 2068402A 2,5-dimethylmandelic acid (65 parts) was reacted with hydroquinone (33 parts) and 98% sulfuric acid (32 parts) and toluene (440 parts) to give 5-hydroxy-2-oxo-3-(2,5-dimethylphenyl)-2,3-dihydrobenzofuran (33 parts) which was isolated by crystallisation and chromatography. The $^1$Hnmr spectrum of the purified product was consistent with structure.

ii) Di-(2-oxo-3-(2,5-dimethylphenyl)-2,3,-dihydrobenzofuran-5-oxy) oxalate

5-Hydroxy-2-oxo-3-(2,5-dimethylphenyl)-2,3-dihydrobenzofuran (2.54 parts), oxalyl chloride (0.64 parts) and 0.37 parts of a 10% w:w solution of 2-dimethylaminopyridine in dichloromethane were added to dichloromethane (53 parts). Under a nitrogen atmosphere, the suspension was heated to reflux temperature for 26 hours. Further oxalyl chloride (0.2 parts) was charged. After 62 hours at reflux temperature, the solution was cooled to ambient temperature, washed with water and the solvent was removed by distillation to give a crude, glass-like product (3.6 parts). Recrystallisation from ethyl acetate gave of di-(2-oxo-3-(2,5-dimethylphenyl)-2,3-dihydrobenzofuran-5-oxy) oxalate (1.17 parts). The $^1$Hnmr spectrum was consistent with structure.

EXAMPLE 17

Preparation of 7-(2,5-Dimethylphenyl)-7-hydro-2,3,6-trioxo-benzo[1:2-b,4:5-b']difuran Di-(2-oxo-3-(2,5-dimethylphenyl)-2,3-dihydrobenzofuran-5-oxy) oxalate (0.8 parts) and triethylamine (0.26 parts) were added to dimethylacetamide (18.7 parts). The solution was heated to 70° C. for 1 hour. The volatiles were removed by distillation (70° C./0.2 mmHg). The product oil (0.96 parts) was analysed using IonSpray lc/ms in negative ion detection mode, which indicated that the major component has an m/e=307 (≡MW of 308) and a fragmentation pattern consistent with 7-(2,5-dimethylphenyl)-7-hydro-2,3,6-trioxo-benzo[1:2-b,4:5-b'] difuran.

EXAMPLE 18

7-Phenyl-7-hydro-2,3,6-trioxo-benzo [1:2-b, 4:5-b'] difuran (2.8 parts) was added to a mixture of glacial acetic acid (45 parts) and sulphuric acid (1.25 parts) with stirring before adding 2-ethylaniline (1.3 parts) and heating under reflux for 90 hours. The reaction mixture was cooled and poured into water (100 parts) and the precipitated solid was collected by filtration, washed with water until acid free and dried at 40° C. to yield 3-phenyl-7-(4-amino-3-ethylphenyl)-2,6-dioxo-2,6-dihydrobenzo-[1:2-b, 4:5-b']-difuran (35%).

EXAMPLE 19

7-Phenyl-7-hydro-2,3,6-trioxo-benzo [1:2-b, 4:5-b'] difuran (2.8 parts) was added to a mixture of 1,2-dichlorobenzene (20 parts), 4-toluenesulphonic acid (1.9 parts) and phenol (1 part) and the mixture was heated at 140°–150° C. for 2½ hours before cooling to ambient temperature. The crystalline solid formed was collected by filtration and was washed with 1,2-dichlorobenzene, methanol, water and methanol again and dried to give 3-phenyl-7-(4-hydroxyphenyl)-2,6-dioxo-2,6-dihydrobenzo-[1:2-b, 4:5-b']-difuran (69.4%).

EXAMPLE 20

7-Phenyl-7-hydro-2,3,6-trioxo-benzo(1:2-b,4:5-b') difuran (2.8 parts) was added to a mixture of glacial acetic acid (47.5 parts) and sulphuric acid (2.5 parts) with stirring before adding 2-ethylaniline (1.3 parts) and heating under reflux for 90 hours. The reaction mixture was cooled and poured into water (100 parts) and the precipitated solid was collected by filtration, washed with water until acid free and dried at 40 deg C. to yield 3-(4-amino-3-ethylphenyl)-7-phenyl-2,6-dioxo-2,6-dihydrobenzo(1:2-b,4:5-b')difuran. (3.8 parts; 100%). After purification λmax 635 nm εmax 38,543 in dimethylformamide.

EXAMPLE 21

7-Phenyl-7-hydro-2,3,6-trioxo-benzo(1:2-b,4:5-b') difuran (2.8 parts) reacted with N:N-diethylaniline (2.25 parts) in o-dichlorobenzene (10 parts) at the reflux for 5 hours. After cooling and dilution with methanol and isolation by filtration to yield 3-(4—N:N-diethylaminophenyl)-7-phenyl-2,6-dioxo-2,6-dihydrobenzo(1:2-b,4:5-b')difuran (1.95 parts; 47.5%). After purification λmax 672 nm εmax 38,559 in dimethylformamide. Analysis C,74.7;H,5.1; N,3.1; C26H21NO4 requires C,75.9; H,5.1; N,3.4%. Mass Spectrometry shows a molecular ion at 411 with fragmentation consistent with structure.

EXAMPLE 22

By the method of Example 20.

7-Phenyl-7-hydro-2,3,6-trioxo-benzo(1:2-b,4:5-b') difuran (2.8 parts) reacted with 2-ethyl 6-methylaniline (1.5 parts) to give 3-(3-methyl-4-amino-5-ethylphenyl)-7-phenyl-2,6-dioxo-2,6-dihydrobenzo(1:2-b,4:5-b')difuran (3.45 parts; 87%). After purification λmax 640 nm εmax 30,462 in dimethylformamide. Mass Spectrometry shows a molecular ion at 397 with fragmentation consistent with structure.

EXAMPLE 23

By the method of Example 20.

7-Phenyl-7-hydro-2,3,6-trioxo-benzo (1:2-b,4:5-b') difuran (0.28 parts) reacted with N-benzyl-o-toluidine (0.25 parts) to give 3-(3-methyl-4-N-benzoylaminophenyl)-7-phenyl-2,6-dioxo-2,6-dihydrobenzo(1:2-b,4:5-b')difuran (0.16 parts). After purification λmax 644.4 nm εmax 42,092 in dimethylformamide. Analysis C,77.2; H,4.6; N,3.0; C30H21NO4 requires C,78.4; H,4.6; N 3.0%. Mass Spectrometry shows a molecular ion at 459 with fragmentation consistent with structure.

EXAMPLE 24

By the method of Example 20.

7-Phenyl-7-hydro-2,3,6-trioxo-benzo(1:2-b,4:5-b') difuran (1.4 parts) reacted with N-ethylaniline (0.74 parts) to give 3-(4-N-ethylaminophenyl)-7-phenyl-2,6-dioxo-2,6-dihydrobenzo(1:2-b,4:5-b')difuran (1.45 parts; 76%). After purification λmax 648 nm εmax 31,365 in dimethylformamide.

EXAMPLE 25

By the method of Example 20.

7-Phenyl-7-hydro-2,3,6-trioxo-benzo(1:2-b,4:5-b') difuran (0.28 parts) reacted with o-cresol (0.15 parts) to give 3-(3-methyl-4-hydroxyphenyl)-7-phenyl-2,6-dioxo-2,6-dihydrobenzo(1:2-b,4:5-b')difuran (0.27 parts; 73%). λmax 523.6 εmax 39,148 in dimethylformamide.

EXAMPLE 26

By the method of Example 20.

7-Phenyl-7-hydro-2,3,6-trioxo-benzo (1:2-b,4:5-b') difuran (0.28 parts) reacted with p-cresol (0.15 parts) to give 3-(2-hydroxy-5-methylphenyl)-7-phenyl-2,6-dioxo-2,6-dihydrobenzo(1:2-b,4:5-b')difuran (0.15 parts). λmax 441.6 nm (broad peak). C,73.6; H,3.8; C23H14O5 requires C,74.6; H,3.8%. Mass Spectrometry shows a molecular ion at 370 consistent with structure. ¹Hnmr spectrum consistent with structure.

EXAMPLE 27

By the method of Example 20.

7-Phenyl-7-hydro-2,3,6-trioxo-benzo(1:2-b,4:5-b') difuran (2.8 parts) was reacted with methoxybenzene (1.5 parts) to give 3-(4-methoxyphenyl)-7-phenyl-2,6-dioxo-2,6-dihydrobenzo(1:2-b,4:5-b')difuran (1.48 parts; 40%). λmax 501 nm εmax 35,530 in dimethylformamide.

EXAMPLE 28

By the method of Example 20.

7-Phenyl-7-hydro-2,3,6-trioxo-benzo (1:2-b,4:5-b') difuran (2.8 parts) was reacted with propoxybenzene (1.5 parts) to give 3-(4-propoxyphenyl)-7-phenyl-2,6-dioxo-2,6-dihydrobenzo(1:2-b,4:5-b')difuran (1.91 parts; 48%). λmax 505 nm εmax 45,100 in dimethylformamide. C,74.6; H,4.3; C25H18O5 requires C,75.4; H,4.5%. Mass Spectrometry shows a molecular ion at 398 with fragmentation consistent with structure.

EXAMPLE 29

Preparation of 3-phenyl-7-(4-hydroxyphenyl)-2,6-dioxo-2,6-dihydro-benzo-[1:2-b, 4:5-b']difuran i) 7-Phenyl-7-H-benzodifuran-2,3,6-trione (2.8 parts) were dissolved in an excess of dilute sodium hydroxide to yield an intensity yellow coloured solution. The solution was acidified by addition of concentrated hydrochloric acid to give an almost colourless solid precipitate which was collected by filtration and washed with water then dried in vacuo over anhydrous calcium chloride. To yield (5-hydroxy-2-oxo-3-phenyl-2,3-dihydrobenzofuran-6-yl)-oxo-acetic acid (2.55 parts).

ii) (5-Hydroxy-2-oxo-3-phenyl-2,3-dihydrobenzofuran-6-yl)-oxo-acetic acid (0.75 parts) were added to a mixture of 1,2-dichlorobenzene (10 parts), p-toluene sulphonic acid 0.5 parts) and phenol (0.3 parts), the reaction mixture was heated to reflux for 2 hours before cooling and examining a sample by thin layer chromatography against an authentic sample of title compound as reference material.

The entire reaction mixture was dissolved in (100 parts) dimethylformamide, diluted appropriately with dimethylformamide and the optical density at 582 nanometers was measured, By comparison with the known molar extinction coefficient of the reference sample the yield of 3-phenyl-7-(4-hydroxyphenyl)-2,6-dioxo-2,6-dihydrobenzo-[1:2-b, 4:5-b']difuran was 67%.

EXAMPLE 30

3-(4-hydroxyphenyl)-7-(4-propoxyphenyl)-2,6-dioxo-2,6-dihydrobenzo (1:2-b,4:5-b')difuran was prepared in a similar manner to Example 30 starting from 7-(4-propoxyphenyl)-7-hydro-2,3,6-trioxobenzo(1:2-b,4:5-b') difuran. Mass spectrometry shows a molecular ion at 414.

EXAMPLE 31

3-(4-hydroxyphenyl)-7-(4-iso propoxyphenyl)-2,6-dioxo-2,6-dihydrobenzo(1:2-b,4:5-b')difuran was prepared in a similar manner to Example 30 starting from 7-(4-iso propoxyphenyl)-7-hydro-2,3,6-trioxobenzo(1:2-b,4:5-b') difuran. Mass spectrometry shows a molecular ion at 414.

EXAMPLE 32

3-(4-N:N-diethylaminophenyl)-7-phenyl-2,6-dioxo-2,6-dihydrobenzo (1:2-b,4:5-b')difuran was prepared in a similar manner to Example 30 starting from 7-phenyl-7-hydro-2,3,6-trioxo-benzo(1:2-b,4:5b')difuran. Mass spectrometry shows a molecular ion at 411.

We claim:

1. A benzodifurantrione of Formula (1):

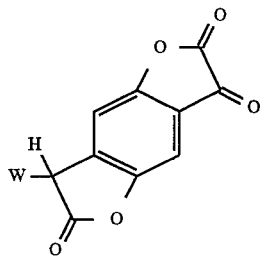   Formula (1)

wherein:

W is unsubstituted or substituted aryl.

2. A benzodifurantrione according to claim 1 in which W is naphthyl or a group of formula:

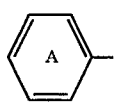

wherein:

Ring A is unsubstituted or substituted by from 1 to 5 groups selected from alkyl; alkenyl; alkoxy; alkoxyalkyl; alkoxyalkoxy; alkylcarbonyl; alkoxycarbonyl; alkoxycarbonylalkoxy; alkoxyalkoxycarbonylalkoxy; alkylcarbonyloxyalkoxy; cyanoalkyl; cyanoalkoxy; hydroxyalkyl; hydroxyalkoxy; haloalkyl; haloalkoxy, alkythio; arylthio; aryloxy; alkylsulphonyl; arylsulphonyl; halo; hydroxy; cyano; nitro; amino; alkylamino; dialkylamino; cycloalkylamino; alkylcarbonylamino; arylcarbonylamino; alkylsulphonylamino; arylsulphonylamino; cycloalkyl; and alkylamino and dialkylamino substituted by —CN, —Cl, —F, —Br, —OH, —COOC$_{1-4}$-alkyl, —COOC$_{1-4}$-alkylOC$_{1-4}$-alkyl,- phenyl, and —OCOC$_{1-4}$-alkyl in which the alkyl or alkoxy contains from 1 to 8 carbon atoms, the alkenyl contains from 2 to 6 carbon atoms, the aryl is phenyl or naphthyl and the cycloalkyl contains from 2 to 6 carbon atoms.

3. A benzodifurantrione according to claim 2 in which Ring A is unsubstituted or is substituted by from 1 to 5 groups selected from C$_{1-4}$-alkyl, C$_{1-4}$-alkoxy, hydroxy, C$_{1-4}$-alkoxy-C$_{1-4}$-alkoxycarbonylC$_{1-4}$-alkoxy, amino, C$_{1-4}$-alkylamino and (C$_{1-4}$-alkyl)$_2$amino and combinations thereof.

4. A process for the preparation of a benzodifurantrione of Formula (1):

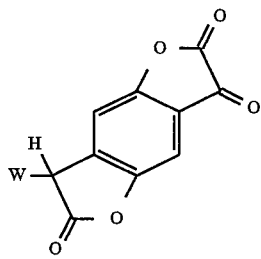   Formula (1)

by reacting a compound of Formula (2):

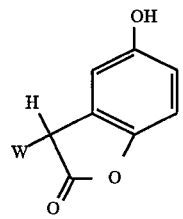   Formula (2)

with a compound of Formula (3):

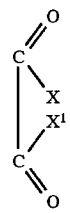   Formula (3)

wherein:

W is unsubstituted or substituted aryl; and X and X$^1$ each independently is halo; —Oalkyl; —OH; —NH$_2$; —NHalkyl and —N(alkyl)$_2$.

5. A process according to claim 4 in which the reaction is carried out in the presence of a non-nucleophilic base.

6. A process according to claim 4 in which the reaction is carried out in the presence of a non-nucleophilic base and an acid binder.

7. A process for the preparation of a benzodifurantrione of Formula (1):

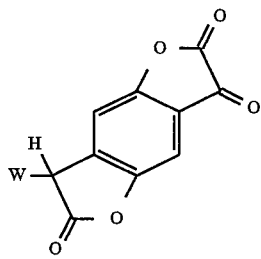   Formula (1)

comprising the steps:

a) Reaction of a compound of Formula (2):

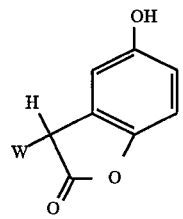   Formula (2)

with a compound of Formula (3):

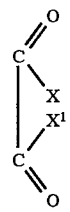   Formula (3)

to form a compound of Formula (4):

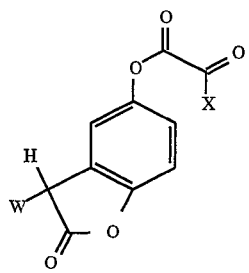

Formula (4)

b) Cyclisation of the compound of Formula (4) to form the benzodifurantrione of Formula (1).

8. A process according to claim 7 wherein step a) is performed in the presence of a non-nucleophilic base.

9. A process according to claim 7 wherein step a) is performed in the presence of a non-nucleophilc base and an acid binder.

10. A process according to claim 7 wherein step b) is performed in the presence of a non-nucleophilic base or in the presence of a Lewis acid.

* * * * *